(12) United States Patent
Munk et al.

(10) Patent No.: US 6,199,257 B1
(45) Date of Patent: Mar. 13, 2001

(54) METHOD OF MAKING A FLOW CELL FOR LIGHT ABSORPTION MEASUREMENT OF SMALL VOLUME SAMPLES (75) Inventors: Miner Nelson Munk, Sonoma, CA (US); Douglas Alan Perry, Palm Beach Gardens; Brian Robert Said, Jupiter, both of FL (US)

(73) Assignee: Thermo Separation Products, Inc., San Jose, CA (US)

( * ) Notice: Subject to any disclaimer, the term of this patent is extended or adjusted under 35 U.S.C. 154(b) by 0 days.

(21) Appl. No.: 08/663,993

(22) Filed: Jun. 14, 1996

Related U.S. Application Data (63) Continuation-in-part of application No. 08/395,784, filed on Feb. 28, 1995, now Pat. No. 5,608,517.

(51) Int. Cl.[7] .................................................. B23P 25/00
(52) U.S. Cl. .............................. 29/423; 427/239; 156/85; 156/293; 264/309; 356/246; 356/440; 29/458
(58) Field of Search ................................ 156/84, 85, 293, 156/294, 309.6; 427/230, 239; 385/125; 356/246; 29/423, 458, 447; 264/299, 300, 309

(56) References Cited

U.S. PATENT DOCUMENTS

| 3,369,426 | * | 2/1968 | Matz, Jr. ............................ 156/294 X |
|---|---|---|---|
| 3,467,098 | * | 9/1969 | Ayers ................................... 385/125 |
| 4,530,569 | | 7/1985 | Squire . |
| 4,575,424 | | 3/1986 | Allington et al. . |
| 4,725,117 | * | 2/1988 | Ellis .................................... 156/84 X |
| 4,754,009 | | 6/1988 | Squire . |
| 4,867,559 | | 9/1989 | Bach . |
| 4,889,611 | | 12/1989 | Blough, Jr. . |
| 4,973,142 | | 11/1990 | Squire . |
| 4,975,505 | | 12/1990 | Squire . |
| 4,977,025 | | 12/1990 | Squire . |
| 4,999,248 | | 3/1991 | Squire . |
| 5,000,547 | | 3/1991 | Squire . |
| 5,006,382 | | 4/1991 | Squire . |
| 5,045,136 | * | 9/1991 | Poulin ................................... 156/85 |
| 5,076,659 | | 12/1991 | Bekiarian et al. . |
| 5,129,979 | * | 7/1992 | Nakayama et al. .................. 156/294 |
| 5,184,192 | | 2/1993 | Gilby et al. . |
| 5,267,341 | | 11/1993 | Shearin . |
| 5,416,879 | | 5/1995 | Liu . |
| 5,444,807 | | 8/1995 | Liu . |
| 5,537,729 | * | 7/1996 | Kolobow .......................... 29/527.1 X |

* cited by examiner

Primary Examiner—S. Thomas Hughes
Assistant Examiner—Marc W. Butler
(74) Attorney, Agent, or Firm—Killworth, Gottman, Hagan & Schaeff, L.L.P.

(57) ABSTRACT

A process for making a flow cell having an internal flow passage of a material having a refractive index less than that of water or having the internal walls of the flow passage coated or otherwise covered with such a material is provided. The flow cell so produced substantially totally internally reflects light along the cell bore.

13 Claims, 5 Drawing Sheets

METHOD OF MAKING A FLOW CELL FOR LIGHT ABSORPTION MEASUREMENT OF SMALL VOLUME SAMPLES

CROSS-REFERENCE TO RELATED APPLICATION

This application is a continuation-in-part of U.S. application Ser. No. 08/395,784, filed Feb. 28, 1995 now U.S. Pat. No. 5,608,517.

BACKGROUND OF THE INVENTION

This invention relates to a process for the manufacture of a flow cell for light absorption measurement, and more particularly, to an improved method for making such a flow cell whose inner wall has an index of refraction less than that of water. The flow cell has special application in the well established techniques of high performance liquid chromatography (HPLC) and capillary zone electrophoresis (CZE).

Light absorption detectors for HPLC and CZE generally comprise four basic components: a light source, a means for selecting a narrow increment of wavelengths, a flow cell, typically in the form of a hollow tube through which a sample to be analyzed and the light are passed, and a light sensor which measures the amount of light transmitted through the flow cell. When a light absorbing component passes through the flow cell, the amount of light transmitted through the flow cell decreases in accordance with Beer's law:

$$\frac{I}{I_0} = 10^{-\alpha BC}$$

where I is the transmitted light power, $I_0$ is the light power incident on the flow cell, $\alpha$ is the molar absorptivity of the sample, B is the path length of the light in the flow cell (in centimeters), and C is the sample concentration (in moles per liter). The detector output is usually in terms of Absorbance (A) which is defined as the product $\alpha$ B C and is proportional to both the sample concentration, C, and the path length, B. The longer the path length, the larger the detector output signal for a given sample concentration.

In conventional flow cells, light that strikes the lateral wall of the flow cell is partially lost due to absorption and scattering at the wall. This lost light causes an increase in noise in the output signal of the detector. The lateral dimension or diameter of the flow cell can be increased to reduce the fraction of light striking the lateral wall, but this increases the volume of the flow cell in proportion to the radius squared. A larger cell volume results in spreading out or dispersion of a sample peak and loss in chromatographic resolution in HPLC and a similar loss in resolution in CZE. In practice, this loss in resolution limits conventional flow cells to path lengths of the order of 6 to 10 mm for HPLC and even shorter for CZE because of the narrower sample peaks or smaller peak volumes associated with CZE.

Accordingly, it has long been desired to produce flow cells capable Qf longer path lengths without an excessive increase in light loss or cell volume. This desire may be realized by providing that the interior wall of the flow cell comprises or is covered with a low refractive index polymer so that light striking the coated wall is totally infernally reflected back into the cell bore, and light-piped along the cell bore. The basic requirement for light-piping (i.e., achieving total internal reflectance of light) is that the refractive index of the interior wall be less than that of the liquid in the flow cell. Water has the lowest refractive index (in the UV range of the spectrum for wavelengths between 190 nm and 300 nm) of liquids commonly used in HPLC and CZE, so the refractive index of the inner wall should be less than that of water. A further requirement of the inner wall is that it be reasonably transparent at the wavelengths used in the measurement of light absorption in the flow cell. While light does not propagate in the inner wall when totally reflected, an evanescent wave is established along the surface that will absorb light power if the wall material is not transparent.

Light-piping in a liquid is not a new concept. Commercial liquid light pipes are available, but these usually contain a high refractive index liquid so that polymer coating of TEFLON® TFE and TEFLON® FEP both of which are available from DuPont Polymers of Wilmington, Del., will effectively pipe light. However, these long available polymers will not effectively pipe light in low refractive index liquids like water as their indices of refraction are greater than that of water.

Recently, new fluoropolymers have become available having indices of refraction which are less than that of water. Such fluoropolymers are available from DuPont as TEFLON® AF. Gilby et al, U.S. Pat. No. 5,184,192, and Liu, U.S. Pat. Nos. 5,416,879 and 5,444,807, all teach flow cells which employ these new fluoropolymers. Liu broadly describes methods of manufacturing such flow cells either by forming the fluoropolymer into rigid tubing or coating the internal walls of a tube with the fluoropolymer. Gilby et al teach alternative methods for forming the flow cells, either by depositing a coating of the fluoropolymer from a solvent or coating the exterior surface of a soluble tube with the fluoropolymer, encapsulating the coated tube in a polymer matrix, and then dissolving the tube.

However, the methods heretofore used in the art have not been entirely successful in producing a flow cell which totally internally reflects light because the large aspect ratio of tube length to tube diameter in combination with the high surface tension of the fluoropolymer makes the coating of the fluoropolymer in the one process and the dissolution of the tube in the other process extremely difficult. Thus, the prior art processes are unable to control either the internal diameter, the surface finish, and the thickness of the material. Accordingly, the need remains for an improved process for the manufacture of a flow cell with walls having an index of refraction lower than that of water and which substantially totally internally reflects light along the cell bore.

SUMMARY OF THE INVENTION

The present invention meets that need by providing a process for making a flow cell having a flow passage, the flow cell including an inner wall which forms the flow passage. The inner wall is made of a material with a refractive index less than that of water or the inner wall is coated or otherwise covered with such a material. All of the internal diameter, the surface smoothness, and the material thickness may be independently controlled to provide a high level of internal light reflectance.

In operation, a liquid phase sample to be analyzed is directed along the flow passage in the flow cell. The flow cell substantially totally internally reflects light along the cell bore. In this manner, light directed into the cell is reflected along the length of the cell through the flow passage, in other words "piped", without substantial loss of light through the walls of the flow passage. As a result, flow cells having longer path lengths and narrower bores may be manufactured permitting greater sensitivity in light absorption detectors.

In accordance with one aspect of the present invention, a process for making a flow cell for light absorption measurement is provided and includes the steps of forming a material having an index of refraction lower than that of water around a process tool and then removing the process tool intact from the material, leaving a flow passage through said material, the flow passage including a first end (where a liquid sample enters) and a second end (where the liquid sample exits the cell). The process tool may be removed by simply pulling it out of the flow passage. First and second light transmission devices, through which light is directed, are positioned adjacent the first and second ends of the flow passage through the material to complete the flow cell.

Preferably, the material is a 1,3 dioxole-4,5 difluoro-2,2 bis trifluoromethyl polymer with tetrafluoroethene. The thickness of the material is independently controllable by coating a sufficient amount on the process tool to assure complete coverage of the surface. The thickness need only be of the order of the wavelengths of light of interest (typically 190 nm to 770 nm) to achieve substantially total internal reflection. Preferably, the thickness is at least about 0.1 mm. Further, the internal dimension and surface texture of the flow passage is independently controlled by choosing the desired dimension and surface texture for the process tool.

A preferred process tool comprises a mandrel. The surface of the mandrel may be polished or otherwise processed to a desired surface smoothness prior to the application of the low index of refraction material around the mandrel. In this manner, the surface smoothness of the flow passage which results when the mandrel is removed is also independently controlled.

In one embodiment, the process includes the step of providing a housing for the flow cell, the housing having an inner cavity which accepts the flow cell and having a first end and a second end. The housing and flow cell are assembled together to define a flow passage having an inlet and an outlet through which a liquid phase sample to be analyzed is directed. The inner wall of the housing is covered with the material by placing the externally coated mandrel into the flow passage of the housing, causing the material to adhere to the housing inner wall, and removing the mandrel intact from the flow passage thereby leaving the material adhered to the inner wall of the housing.

In another embodiment, the process tool is a die, and the step of forming the material around the process tool includes the step of extruding the material through the die to form a housing having an inner wall defining the flow passage. In yet another embodiment, the process tool is a mandrel insert, and the step of forming the material around a process tool includes the steps of heating the material, casting the material around the mandrel insert in a die to form a housing having an inner wall defining the flow passage, cooling the material, and removing the housing from the die and the mandrel insert from the housing.

In yet a further embodiment, the process tool is a mandrel insert, and the step of forming the material around the process tool includes the steps of heating the material, injecting the material into a mold and around the mandrel insert positioned in the mold to form a housing having an inner wall defining the flow passage, cooling the material, and removing the housing from the mold and the mandrel insert from the housing.

The flow cell produced by the process of the present invention may have a flow passage of about 10 mm or longer while having an aperture of less than about 1 mm. Preferably, the flow cell is at least about 50 mm in length while having an aperture of less than about 1 mm. The flow cell is capable of internally reflecting or "piping" at least about 80% and preferably 90% or greater of the light directed into the flow passage.

Accordingly, it is a feature of the present invention to provide a process for making a flow cell having an internal flow passage of a material having a refractive index less than that of water or having the internal walls of the flow passage coated or otherwise covered with such a material. It is a further feature of the invention to provide a controlled dimension for the flow passage and to provide the surface of the material with a degree of smoothness which results in high internal reflectance of light directed along the flow passage. These, and other features and advantages of the present invention, will become apparent from the following detailed description, the accompanying drawings, and the appended claims.

DETAILED DESCRIPTION OF THE PREFERRED EMBODIMENTS

Figure 1:
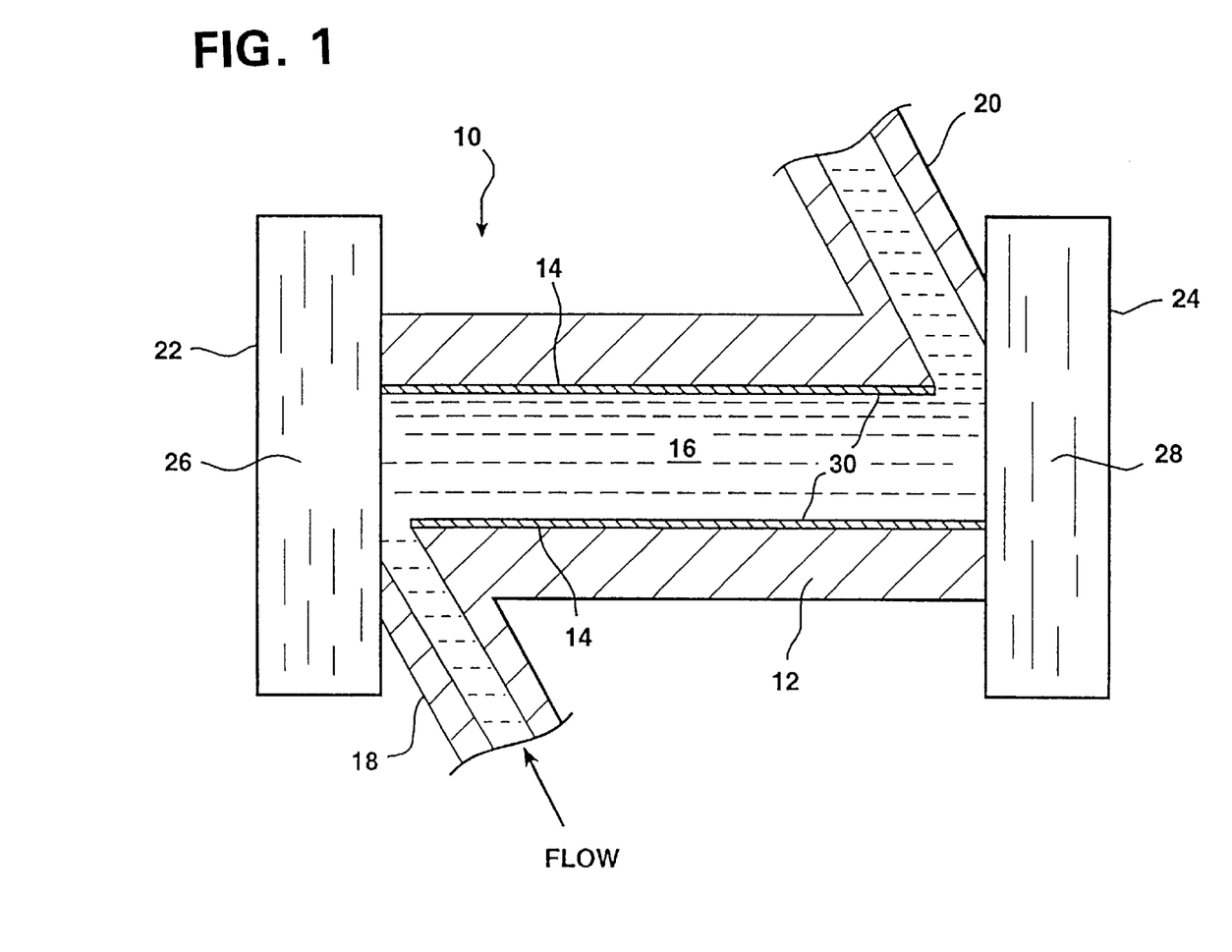
FIG. 1 is schematic view of the coated flow cell manufactured according to the process of the present invention.

The present invention provides a process for making a flow cell that is superior in directing light from a source through a sample and to a detector with little or no loss of light due either to absorption or scattering along the walls of the flow passage through the cell. Turning to FIG. 1, the flow cell 10 which results from the manufacturing process of the present invention is depicted. Flow cell 10 comprises a housing 12 having an inner wall 14 defining a flow passage 16.

Typically, but not necessarily, flow passage 16 will be a cylindrically-shaped bore. Because of the unique manner in which the flow cell is fabricated, the diameter of the bore is independently and closely controlled through the manufacture of the process tool. Flow cell 10 includes an inlet 18 through which a sample to be analyzed enters flow passage 16. The flow cell 10 also includes an outlet 20 through which the sample exits the flow cell 10. One of ordinary skill in the art will recognize that flow cell 10 can take various other shapes and geometries besides that depicted in FIG. 1.

The housing 12 of flow cell 10 also includes a first end 22 and a second end 24. First end 22 includes a first light transmission device such as, for example, transparent window 26 through which light is directed into the flow passage 16 from a source (not shown). Second end 24 also includes a second light transmission device such as transparent window 28 through which light departs the flow passage 16. Transparent windows 26 and 28 may be constructed of any suitable material, such as quartz, fused silica or transmitting optical fibers which is known in the art for providing transparency. Furthermore, transparent-windows 26 and 28 may be of any size or shape known in the art, such as a slit.

Of course, one of ordinary skill in the art will recognize that the size, shape or material, used in transparent windows 26 and 28 will depend upon end use considerations as well as the detector into which the flow cell is incorporated. It will be further recognized that other light transmitting devices such as fiber optics may be positioned adjacent opposite ends of the flow passage in place of or in addition to the transparent windows which are depicted.

Material 30, having an index of refraction lower than that of water, is present on inner wall 14 of housing 12. As a result, light which is directed into the flow passage 16 at angles up to a certain acceptance angle is totally internally reflected by the inner wall 14. The light is reflected down the length of flow passage 16, or in other words, the light is piped. In this fashion, substantially less light is lost through the walls of the housing than in conventional flow cells. Flow cell 10 internally reflects or pipes at least about 80% of the light directed into the flow passage 16, and preferably at least about 90% or more of the light transmitted into the flow cell. Preferably material 30 has a thickness greater than at least about 0.1 mm to assure complete coverage.

Since flow cell 10 pipes light down the flow passage 16, substantially longer and narrower flow passages or path lengths are possible. Further, as light is piped down the flow passage, there is no requirement that the flow passage be straight as in prior art flow cells. Rather, the flow passages of cell 10 may contain curves or bends, thereby contributing advantages to detector design.

Increased sensitivity is gained without a substantial increase in background noise or substantial loss of peak resolution in the detector. Flow passages 16 which are 10 mm or greater in length, with bore diameters of less than about 1 mm, preferably about 0.5 mm, are achievable. Preferably, the flow passage is at least 25 mm in length while having a diameter of less than about 1 mm. More preferably, the flow passage is at least about 50 mm in length while having a diameter of at less than about 1 mm.

Returning to FIG. 1, material 30 has an index of refraction lower than that of water. Water has a lower refractive index than other solvents commonly used in HPLC and CZE for UV wavelengths of primary interest, i.e., wavelengths between 190 nm and 300 nm. If light of these wavelengths can be light piped through a flow cell filled with water, it can be light piped with other common carrier liquids used in the art as well.

Suitable materials include polymers having an index of refraction below that of water such as 1,3 dioxole-4,5 difluoro-2,2 bis trifluoromethyl polymers with tetrafluoroethene, available from Dupont Polymers of Wilmington, Del. under the trademark TEFLON® AF. This family of polymers is described in Squire, U.S. Pat. No. 5,006,382 and Bekarian et al, U.S. Pat. No. 5,076,659, among others. Two versions of TEFLON® AF include TEFLON® AF 1600 with an index of refraction of 1.305 at a wavelength of 589 nm and TEFLON® AF 2400 with an index of refraction of 1.294 at a wavelength of 589 nm. TEFLON® AF is transparent both to ultraviolet and visible light and is suitable for standard thermoplastic processing.

As a result of the piping of light, the flow cell provides for superior acceptance of incident half angles of light. The incident half angle of light is the half angle at which light may be directed into the first transparent window 26. In other words, it is the half angle at which light may be directed into flow passage 16. The expression determining light piping is:

$$\sin \theta_0 < \sqrt{n_L^2 - n_C^2}$$

where $\theta_0$ is the half angle of incidence of the light entering the first transparent window, $n_L$ is the refractive index of the liquid in the cell and $n_C$ is the refractive index of the inner wall of the flow cell. As $n_L$ for the present invention is greater than $n_C$, it can be seen from FIG. 4 that light 40 will be internally reflected or piped down the length of flow passage 16. It can also be seen that the flow cell 10 will accept much greater incident half angles of light $\theta_0$ in the narrower cell widths preferred for the present invention than prior art cells of the same geometry. Due to loss of light, prior art flow cells of similar narrow bore geometry must have light enter the flow cell almost parallel to the flow passage, at an incident half angle of 0.5° or less. Whereas, flow cell 10 may accept incident half angles of light $\theta_0$ of at least about 10°, and preferably of at least about 15°. As a result, a significantly greater amount of the light entering flow passage 16 is directed through that flow passage than in prior art flow cells, thereby increasing sensitivity. Furthermore, more flexibility in detector design is provided.

Flow cell 10 may be employed in conventional light absorption detectors known in the art such as, for example, UV/visible monochromatic detectors employing a photo-diode detector as well as UV/visible polychromatic detectors employing diode array detectors. However, due to a desire for narrower cell bores for use with diode array detectors, flow cell 10 is highly suited for use in conjunction with diode array detectors. Flow cell 10 may also be used in conjunction with fluorescence detectors, calorimeters, Raman scattering spectroscopy, as well as in other systems involving liquid chromatography and capillary electrophoresis.

A preferred process for coating the flow cell is shown in FIGS. 2a–2d. Returning to FIG. 2a, a mandrel 80 externally coated with a polymer 82, such as TEFLON® AF, having an index of refraction lower than that of water is provided. Mandrel 80 is generally cylindrical and may be constructed of a material that can be polished to a smooth finish. Preferably, mandrel 80 also has reasonable mechanical strength and integrity at temperatures consistent with the processing of the low refractive index materials used. Preferably, the mandrel is a chemically inert material such as a plastic or a corrosion-resistant metal alloy (for example, stainless steel), and the mandrel is removed from the formed wall structure by pulling it out of bore. In this case a slightly tapered mandrel can be used to facilitate the pulling out of the mandrel.

Figure 2A:
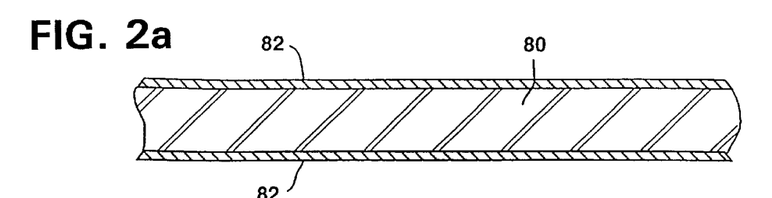
FIGS. 2a–2d are schematic representations of the steps of a preferred process for manufacturing the flow cell of the present invention.

The mandrel can be coated by dipping and drying of the mandrel into a solution of TEFLON® AF dissolved in FLUORINERT® solvent. When a sufficient thickness of TEFLON® AF has been deposited, the coating is thermally cured and then slowly cooled to ambient temperature. In this manner, the thickness of the material is independently controlled to be within desired tolerances. Further, by polishing the surface of the mandrel, the surface smoothness of the wall of the material may also be controlled independently of material thickness as the material will assume substantially the same degree of surface smoothness as the polished surface it is deposited on. That is, the surface smoothness of the material at the material/mandrel interface is itself very smooth.

Figure 2B:
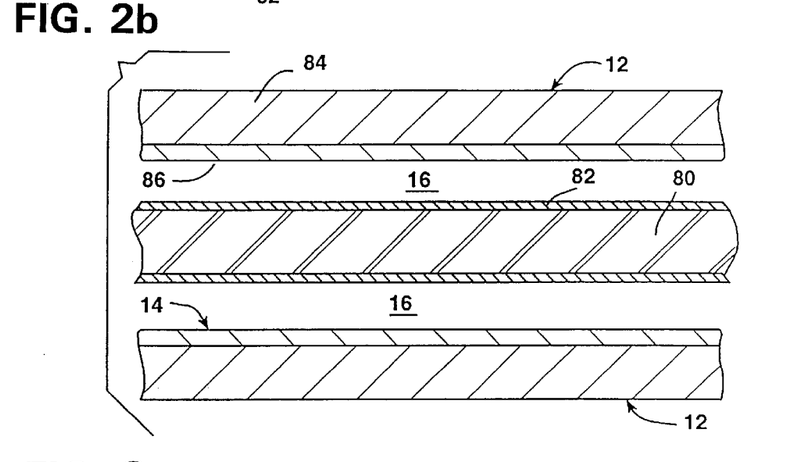

Turning next to FIG. 2b, coated mandrel 80 is inserted into a cavity in housing 12 which will form flow passage 16. Housing 12, in this embodiment of the invention, comprises heat shrinkable, polytetrafluoroethylene tubing. Housing 12 may also comprise a dual heat-shrink tubing. Thus, in a preferred embodiment, the housing comprises an outer layer 84 of tetrafluoroethylene homopolymer, known as TEFLON-TFE® available from DuPont Polymers of Wilmington, Del. and an inner layer 86 of tetrafluoroethylene copolymer with hexafluoropropylene, known as TEFLON-FEP®, also available from DuPont Polymers, as inner wall 14.

Figure 2C:
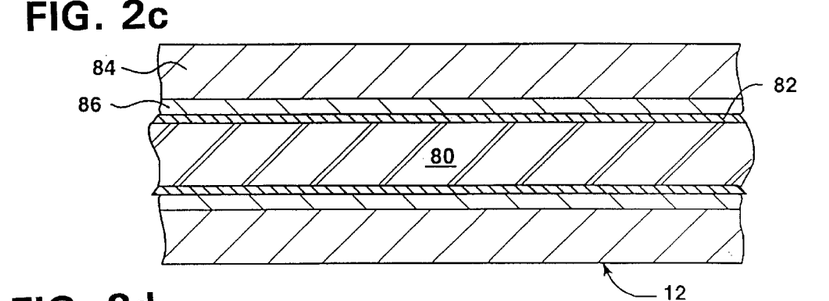
Figure 2D:
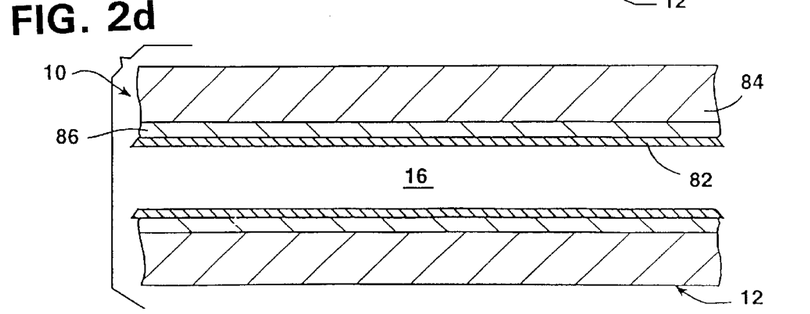
Figure 3:
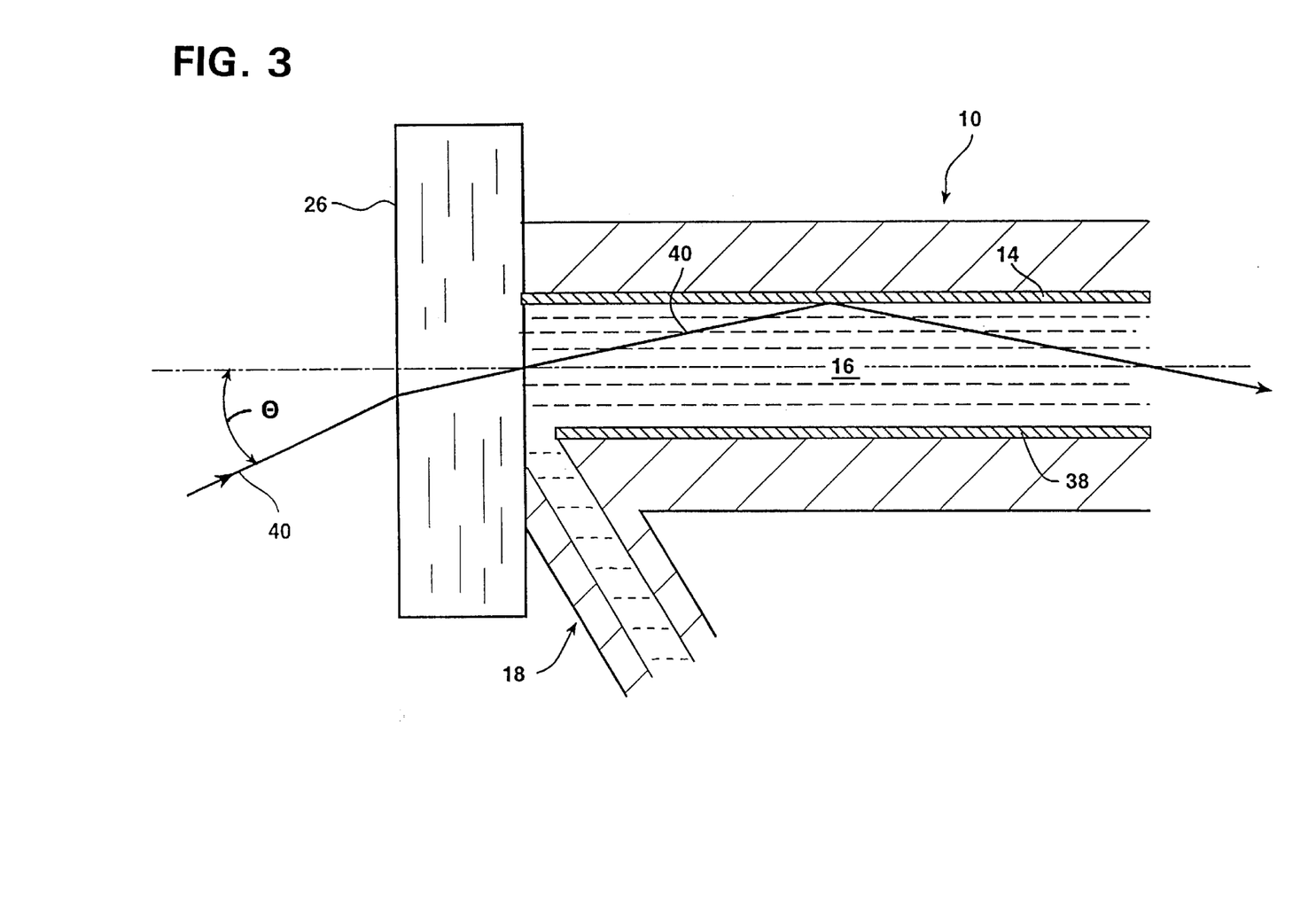
FIG. 3 is a schematic view of light entering the flow cell.

A suitable assembly is then heated to shrink the outer layer 84 and to melt the inner layer 86. The melting inner layer 86 fuses to the polymer layer 82 on mandrel 80 upon cooling, as shown in FIG. 2c. Mandrel 80 is then removed from flow passage 16 as shown in FIG. 2d, leaving polymer layer 82 fused and bonded to inner layer 86. The heating and heat-shrinking steps produce a flow of polymer layer 82.

Further, the pressure applied by the heat-shrink tubing also produces a strong mechanical bond between the layers to hold polymer layer 82 in position. During the heat shrinking steps, it may be desirable to shape the ends of housing 12 to provide a proper fit for end seals on the tubing. The end product, once assembled and sealed, is a flow cell 10 internally coated with a polymer having an index of refraction lower than that of water which acts as a light pipe.

In an alternative embodiment of the invention, the process of making the flow cell utilizes thermoplastic polymer extrusion techniques. In this embodiment, the process tool comprises a two-part die in which the inner and outer portions of the die form an annular opening through which the heated low index of refraction material is extruded. The opening between die parts establishes a precise inner diameter for the extrudate as well as a precise thickness. Moreover, the surfaces of the dies may be polished to impart a high degree of surface smoothness to the extrudate. The step of forming the material around the process tool includes the step of extruding the material through the die to form a housing having an inner wall of a precise inner diameter defining the flow passage.

Figure 4A:
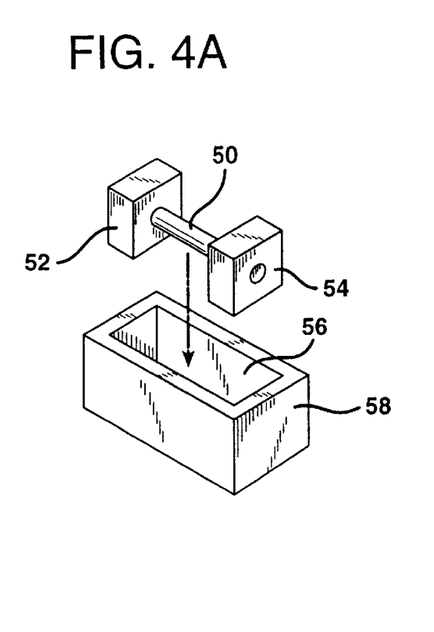
FIGS. 4a–4c are schematic representations of the steps of a preferred process for casting the housing of the flow cell.
Figure 4B:
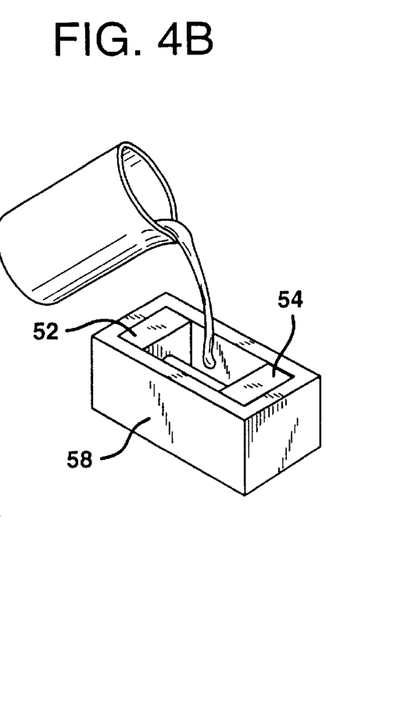
Figure 4C:
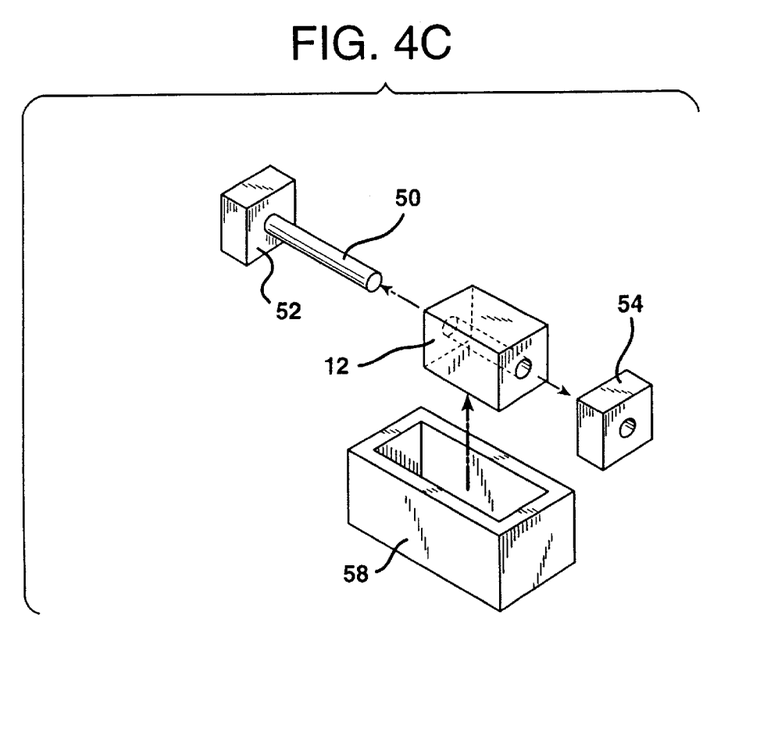

In another embodiment of the invention illustrated in FIGS. 4a–4c, the housing 12 for the flow cell is manufactured using casting techniques. As schematically shown in FIG. 4a, the process tool is a mandrel 50, the ends of which are fitted into blocks 52 and 54. Blocks 52 and 54 may be fabricated of any suitable material which will not melt during the casting process. Mandrel 50, with blocks 52 and 54 attached, is positioned in a cavity 56 of a casting mold 58. As shown in FIG. 4b, low index of refraction material 30 is heated to a liquid state, and the material is then poured into cavity 56 of mold 58 and around mandrel 50 to form a casting. Once solidified and cooled, the casting is removed from the cavity, and mandrel 50 is removed from the casting, forming housing 12 having an inner wall defining the flow passage through the flow cell.

Figure 5:
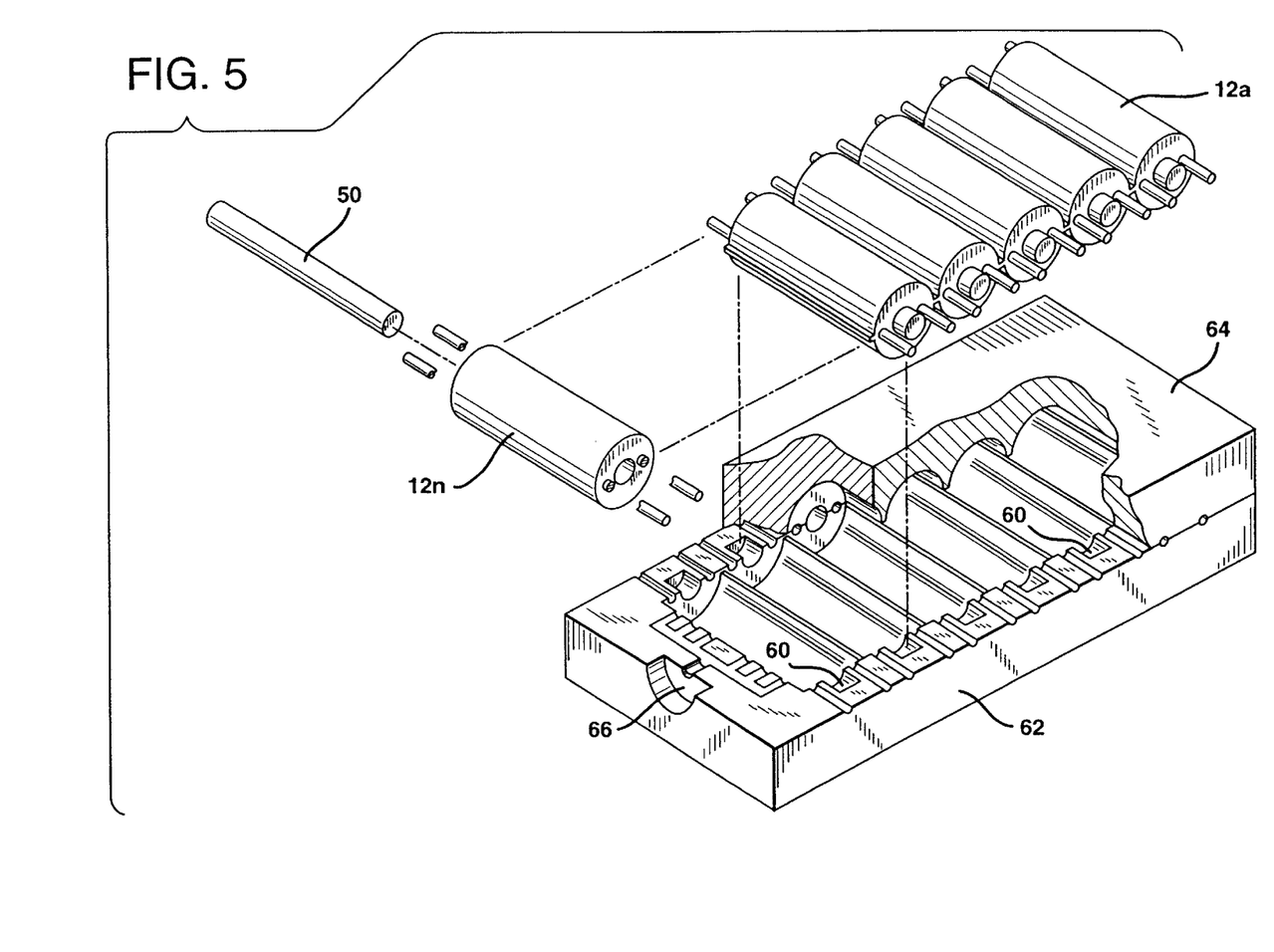
FIG. 5 is a schematic representation of a preferred process for molding the housing of the flow cell.

In another embodiment of the invention, housing 12 may be manufactured using molding techniques, for example injection molding. In this embodiment as schematically shown in FIG. 5, the process tool is again mandrel 50. A mold is formed using a pair of mold halves 62, 64 which can be opened and closed in a conventional manner. To produce a series of housings 12a–12n, mandrels 50 are laid in spaced relationship in grooves 60 along the length of mold half 62, and mold half 64 is then positioned on top of mold half 62. Low index of refraction material 30 is heated and then injected or otherwise is made to flow through opening 66 in the mold as internal gas is vented through risers 67. Material 30 then flows around the series of mandrels 50 to form the series of housings 12a–12n. Each housing 12 has an inner wall defining the flow passage. Once the material is cooled and hardened, the mold is opened, and the series of housings are removed from the mold. The housings may then be separated one from another and from each runner 68, and the mandrels 50 removed.

In another embodiment of the invention, housing 12 is formed by extruding the low index of refraction material, typically in the form of a cylinder of desired length. As the preferred fluorocarbon polymer (TEFLON® AF) is melt processable, the extrusion may be a melt extrusion process. Alternatively, cold extrusion or semi-solid forging techniques may be utilized to form the housing. Alternatively, the housing may be formed by casting the low refractive index polymeric material in a mold or by an injection molding process. For this embodiment of the invention, flow passage 16 through the housing is created by drilling a bore of appropriate diameter through the housing in a secondary manufacturing operation. To provide both a uniform diameter bore, as well as a bore whose internal wall has the requisite degree of smoothness, a number of precision boring, drilling, or cutting techniques may be used including laser boring, electron beam boring, thermal boring, machine boring, mechanical drilling (rotary cutting, precision reaming, fluid honing), and hydraulic boring.

In yet a further embodiment of the invention, the low index of refraction material may be deposited on the inner wall of housing 12 by a heated atomized spray.

Having described the invention in detail and by reference to the preferred embodiment thereof, it will be apparent that modifications and variations are possible without departing from the scope of the invention which is defined in the appended claims.

What is claimed is:

1. A process for making a flow cell for light absorption measurement comprising the steps of:

forming a predetermined thickness of a material having an index of refraction lower than that of water around a process tool having a predetermined diameter and a controlled surface smoothness such that the surface smoothness, inner diameter, and wall thickness of said material are consistently controlled;

removing said process tool intact from said material leaving a flow passage through said material, said flow passage including first and second ends; and positioning first and second light transmission devices through which light is directed adjacent said first and second ends of said flow passage such that said material internally reflects at least about 80% of the light directed into said flow passage.

2. A process as claimed in claim 1 wherein said step of removing said process tool intact comprises pulling said process tool from said flow passage.

3. A process as claimed in claim 1 wherein said material comprises 1,3 dioxole-4,5 difluoro-2,2 bis trifluoromethyl polymer with tetrafluoroethene.

4. A process as claimed in claim 1 in which said process tool comprises a mandrel, and the step of forming said material around said process tool comprises coating the exterior surface of said mandrel with said material.

5. A process as claimed in claim 4 wherein said mandrel is polished before said material is externally coated onto said mandrel.

6. A process as claimed in claim 4 including the step of providing a housing for said flow cell, said housing having an inner cavity and an inner wall which accepts said flow cell, said housing further having a first end and a second end; and internally coating said inner wall of said housing with said material by placing said externally coated mandrel into said inner cavity of said housing, causing said material to adhere to said housing inner wall, and removing said mandrel from said cavity thereby leaving said material adhered to said inner wall of said housing and forming said flow cell with a flow passage having an inlet and an outlet through which a liquid phase sample to be analyzed is directed.

7. A process as claimed in claim 6 wherein said housing comprises a hollow polytetrafluoroethylene tube.

8. A process for making a flow cell for light absorption measurement comprising the steps of:

providing a housing for said flow cell, said housing having an inner cavity and an inner wall which accepts said flow cell, said housing further having a first end and a second end and wherein said housing comprises a hollow tube including a polytetrafluoroethylene outer layer and a copolymer of tetrafluoroethylene and hexafluoropropylene inner layer;

coating a predetermined thickness of a material having an index of refraction lower than that of water around the exterior surface of a mandrel having a predetermined diameter and a controlled surface smoothness such that the surface smoothness, inner diameter, and wall thickness of said material are consistently controlled;

internally coating said inner wall of said housing with said material by placing said externally coated mandrel into said inner cavity of said housing, causing said material to adhere to said housing inner wall;

removing said mandrel intact from said cavity thereby leaving said material adhered to said inner wall of said housing and forming said flow cell with a flow passage having an inlet and an outlet through which a liquid phase sample to be analyzed is directed; and positioning first and second light transmission devices through which light is directed adjacent said first and second ends of said flow passage such that said material internally reflects at least about 80% of the light directed into said flow passage.

9. A process as claimed in claim 6 wherein said step of causing said material to adhere to said housing wall comprises applying heat to said housing.

10. A process for making a flow cell for light absorption measurement comprising the steps of:

providing a housing for said flow cell, said housing having an inner cavity and an inner wall which accepts said flow cell, said housing further having a first end and a second end and wherein said housing comprises a hollow tube including a polytetrafluoroethylene outer layer and a copolymer of tetrafluoroethylene and hexafluoropropylene inner layer;

coating a predetermined thickness of a material having an index of refraction lower than that of water around the exterior surface of a mandrel having a predetermined diameter and a controlled surface smoothness such that the surface smoothness, inner diameter, and wall thickness of said material are consistently controlled;

internally coating said inner wall of said housing with said material by placing said externally coated mandrel into said inner cavity of said housing, causing said material to adhere to said housing inner wall;

removing said mandrel intact from said cavity thereby leaving said material adhered to said inner wall of said housing and forming said flow cell with a flow passage having an inlet and an outlet through which a liquid phase sample to be analyzed is directed; and positioning first and second light transmission devices through which light is directed adjacent said first and second ends of said flow passage such that said material internally reflects at least about 80% of the light directed into said flow passage, and wherein said step of causing said material to adhere to said housing wall comprises applying heat to said housing to shrink said outer layer of polytetrafluoroethylene and melt said inner layer of said copolymer of tetrafluoroethylene and hexafluoropropylene.

11. A process as claimed in claim 1 wherein said process tool is a die, and the step of forming said material around said process tool includes a step of extruding said material through said die to form a housing having an inner wall defining said flow passage.

12. A process as claimed in claim 1 wherein said process tool is a mandrel insert, and the step of forming said material around said process tool includes steps of heating said material, casting said material around said mandrel insert in a die to form a housing having an inner wall defining said flow passage, cooling said material, removing said housing from said die, and removing said mandrel insert from said housing leaving said flow passage through said material.

13. A process as claimed in claim 1 wherein said process tool is a mandrel insert, and the step of forming said material around said process tool includes steps of heating said material, injecting said material into a mold and around said mandrel insert positioned in said mold to form a housing having an inner wall defining said flow passage, cooling said material, removing said housing from said mold, and removing said mandrel insert from said housing leaving said flow passage through said material.

* * * * *

UNITED STATES PATENT AND TRADEMARK OFFICE
CERTIFICATE OF CORRECTION

PATENT NO. : 6,199,257 B1  
DATED : March 13, 2001  
INVENTOR(S) : Miner Nelson Munk; Douglas Alan Perry; Brian Robert Said Page 1 of 1

It is certified that error appears in the above-identified patent and that said Letters Patent is hereby corrected as shown below:

Column 1,  
Line 58, "capable Qf longer" should be -- capable of longer --.  
Line 62, "totally infernally" should be -- totally internally --.

Column 2,  
Line 15, "Wilmington, Del.," should be -- Wilmington, Delaware, --.

Column 5,  
Line 2, "shape or material, used" should be -- shape or material used --.  
Line 48, "Wilmington, Del." should be -- Wilmington, DE --.  
Line 65, "$\sin \theta_0 < \sqrt{n_L^2 - n^2 c}$" should be -- $\sin \theta_0 < \sqrt{n_L^2 - n_c^2}$ --.

Column 6,  
Line 66, "Wilmington, Del." should be -- Wilmington, DE --.

Signed and Sealed this

Sixteenth Day of October, 2001

Attest:

NICHOLAS P. GODICI  
Attesting Officer  
Acting Director of the United States Patent and Trademark Office